US012702570B2

(12) United States Patent
Yoko et al.

(10) Patent No.: US 12,702,570 B2
(45) Date of Patent: Aug. 11, 2026

(54) IMPACTION CRADLE

(71) Applicant: Zimmer, Inc., Warsaw, IN (US)

(72) Inventors: Tim Yoko, Granger, IN (US); Amanda Szalkowski, Winona Lake, IN (US); Jeffery A. VanDiepenbos, New Paris, IN (US)

(73) Assignee: Zimmer, Inc., Warsaw, IN (US)

( * ) Notice: Subject to any disclaimer, the term of this patent is extended or adjusted under 35 U.S.C. 154(b) by 879 days.

(21) Appl. No.: 17/733,768

(22) Filed: Apr. 29, 2022

(65) Prior Publication Data

US 2022/0249251 A1 Aug. 11, 2022

Related U.S. Application Data

(63) Continuation of application No. 16/652,896, filed as application No. PCT/US2018/055218 on Oct. 10, 2018, now Pat. No. 11,351,041.

(Continued)

(51) Int. Cl.
*A61F 2/46* (2006.01)
*A61F 2/38* (2006.01)

(52) U.S. Cl.
CPC ............ *A61F 2/461* (2013.01); *A61F 2/3859* (2013.01); *A61F 2/389* (2013.01); *A61F 2002/4681* (2013.01)

(58) Field of Classification Search
CPC ..... A61B 17/157; A61B 17/155; A61B 17/15; A61B 17/1725; A61B 17/1739;

(Continued)

(56) References Cited

U.S. PATENT DOCUMENTS 4,751,922 A 6/1988 Dipietropolo
5,282,861 A 2/1994 Kaplan (Continued)

FOREIGN PATENT DOCUMENTS

AU 2023202761 2/2025
CN 101744675 A 6/2010

(Continued)

OTHER PUBLICATIONS

"U.S. Appl. No. 16/047,463, Corrected Notice of Allowability mailed Mar. 31, 2021", 2 pgs.

(Continued)

*Primary Examiner* — Melanie R Tyson
*Assistant Examiner* — Paris Marie Blass
(74) *Attorney, Agent, or Firm* — Schwegman Lundberg & Woessner, P.A.

(57) ABSTRACT

An impaction cradle (50) for supporting a femoral (10) or tibial (70) implant on a planar support surface such as a tabletop. The impaction cradle can orient the femoral or tibial implant on the impaction cradle such that an attachment feature of the implant for an intramedullary stem or metaphyseal sleeve is aligned with a vertical plane or parallel to the true vertical axis. In this position, the intramedullary stem or metaphyseal sleeve can be impacted along a generally vertical axis to drive the intramedullary stem or metaphyseal sleeve along an impaction axis parallel to a true vertical axis or positioned within a vertical plane. The generally vertical impaction angle can be easier for medical practitioners to accurately impact the intramedullary stem or metaphyseal sleeve, which lowers the risk of damage to the intramedullary stem, metaphyseal sleeve, or the femoral or tibial implant.

15 Claims, 13 Drawing Sheets

Related U.S. Application Data

(60) Provisional application No. 62/570,889, filed on Oct. 11, 2017.

(58) Field of Classification Search
CPC . A61B 17/1764; A61B 5/4528; A61B 5/4851; A61F 2/461; A61F 2/3859; A61F 2/389; A61F 2002/4681; A61F 2/46; A61F 2/3836; B33Y 80/00
See application file for complete search history.

(56) References Cited

U.S. PATENT DOCUMENTS

| | | | | |
|---|---|---|---|---|
| 5,702,461 | A | 12/1997 | Pappas et al. | |
| 6,159,216 | A | 12/2000 | Burkinshaw et al. | |
| 6,171,342 | B1 | 1/2001 | O'Neil et al. | |
| 6,258,093 | B1 | 7/2001 | Edwards et al. | |
| 6,902,583 | B2 | 6/2005 | Gerbec et al. | |
| 6,911,100 | B1 | 6/2005 | Gibbs et al. | |
| 7,291,174 | B2 | 11/2007 | German et al. | |
| 7,799,085 | B2 | 9/2010 | Goodfried et al. | |
| 8,187,280 | B2 | 5/2012 | May et al. | |
| 8,535,385 | B2 | 9/2013 | Hanssen et al. | |
| 8,556,900 | B2 | 10/2013 | Yoko et al. | |
| 8,721,733 | B2 | 5/2014 | Bonitati | |
| 8,979,847 | B2 | 3/2015 | Belcher et al. | |
| 8,998,996 | B2 | 4/2015 | James et al. | |
| 9,603,649 | B2 | 3/2017 | Matyas et al. | |
| 10,182,830 | B2 | 1/2019 | Amanatullah | |
| 10,987,225 | B2 | 4/2021 | Yoko et al. | |
| 11,141,290 | B2 | 10/2021 | Yoko et al. | |
| 11,351,041 | B2 | 6/2022 | Yoko et al. | |
| 2003/0050643 | A1 | 3/2003 | Taft | |
| 2003/0097133 | A1 | 5/2003 | Green et al. | |
| 2003/0158606 | A1* | 8/2003 | Coon | A61F 2/38 623/20.15 |
| 2004/0049286 | A1 | 3/2004 | German et al. | |
| 2005/0107886 | A1* | 5/2005 | Crabtree | A61F 2/385 623/20.29 |
| 2005/0124998 | A1 | 6/2005 | Coon et al. | |
| 2005/0177122 | A1 | 8/2005 | Berba et al. | |
| 2006/0241635 | A1 | 10/2006 | Stumpo et al. | |
| 2007/0101827 | A1 | 5/2007 | Quan et al. | |
| 2009/0149964 | A1* | 6/2009 | May | A61B 17/1764 623/20.29 |
| 2009/0270927 | A1 | 10/2009 | Perrow et al. | |
| 2009/0306787 | A1 | 12/2009 | Crabtree et al. | |
| 2010/0063507 | A1 | 3/2010 | Sidebotham et al. | |
| 2011/0029090 | A1* | 2/2011 | Zannis | A61F 2/389 623/20.28 |
| 2011/0082559 | A1* | 4/2011 | Hartdegen | A61F 2/389 623/20.32 |
| 2012/0143204 | A1 | 6/2012 | Blaylock et al. | |
| 2012/0245700 | A1 | 9/2012 | Sidebotham | |
| 2012/0310246 | A1 | 12/2012 | Belcher et al. | |
| 2013/0006370 | A1 | 1/2013 | Wogoman et al. | |
| 2013/0172892 | A1 | 7/2013 | Servidio et al. | |
| 2013/0304221 | A1 | 11/2013 | Blaylock et al. | |
| 2013/0325019 | A1 | 12/2013 | Thomas et al. | |
| 2014/0228846 | A1 | 8/2014 | Roby et al. | |
| 2014/0276838 | A1 | 9/2014 | Tsukayama et al. | |
| 2014/0276859 | A1 | 9/2014 | Chaney et al. | |
| 2014/0277528 | A1 | 9/2014 | Mines et al. | |
| 2014/0277540 | A1 | 9/2014 | Leszko et al. | |
| 2014/0277546 | A1 | 9/2014 | Major et al. | |
| 2015/0127005 | A1 | 5/2015 | Mcmanus | |
| 2015/0190150 | A1 | 7/2015 | Primiano et al. | |
| 2015/0216667 | A1 | 8/2015 | Monaghan | |
| 2016/0081758 | A1 | 3/2016 | Bonutti | |
| 2016/0367381 | A1 | 12/2016 | Chaney et al. | |
| 2017/0000503 | A1 | 1/2017 | Keefer et al. | |
| 2017/0172748 | A1 | 6/2017 | Angibaud et al. | |
| 2017/0231642 | A1 | 8/2017 | Chaney et al. | |
| 2017/0281199 | A1 | 10/2017 | Amanatullah | |
| 2019/0038417 | A1 | 2/2019 | Yoko et al. | |
| 2019/0105159 | A1 | 4/2019 | Dees et al. | |
| 2019/0110906 | A1 | 4/2019 | Yoko et al. | |
| 2019/0110907 | A1 | 4/2019 | Yoko et al. | |
| 2020/0289290 | A1 | 9/2020 | Yoko et al. | |
| 2021/0353436 | A1 | 11/2021 | Yoko et al. | |
| 2022/0249251 | A1 | 8/2022 | Yoko et al. | |
| 2026/0069435 | A1 | 3/2026 | Yoko et al. | |

FOREIGN PATENT DOCUMENTS

| | | | |
|---|---|---|---|
| CN | 104013456 | A | 9/2014 |
| CN | 104042303 | A | 9/2014 |
| CN | 104042368 | A | 9/2014 |
| CN | 104042369 | A | 9/2014 |
| CN | 111212616 | A | 5/2020 |
| CN | 114652492 | | 6/2022 |
| EP | 0440371 | | 8/1991 |
| EP | 4248886 | | 3/2026 |
| JP | H05103790 | | 4/1993 |
| JP | H08506260 | | 7/1996 |
| JP | 2008515498 | | 5/2008 |
| JP | 2014176658 | A | 9/2014 |
| JP | 2020536670 | A | 12/2020 |
| JP | 7125480 | | 8/2022 |
| JP | 2022140793 | | 9/2022 |
| JP | 7450676 | | 3/2024 |
| JP | 2024059963 | | 5/2024 |
| JP | 7699683 | B2 | 6/2025 |
| JP | 2025120473 | A | 8/2025 |
| WO | WO-03045257 | A2 | 6/2003 |
| WO | 2012021779 | | 2/2012 |
| WO | WO-2013086340 | A1 | 6/2013 |
| WO | WO-2013102089 | A1 | 7/2013 |
| WO | WO-2014063084 | A1 | 4/2014 |
| WO | WO-2019075066 | A1 | 4/2019 |
| WO | WO-2019075078 | A1 | 4/2019 |

OTHER PUBLICATIONS

"U.S. Appl. No. 16/047,463, Final Office Action mailed Sep. 4, 2020", 15 pgs.
"U.S. Appl. No. 16/047,463, Non Final Office Action mailed Feb. 21, 2020", 18 pgs.
"U.S. Appl. No. 16/047,463, Notice of Allowance mailed Dec. 14, 2020", 5 pgs.
"U.S. Appl. No. 16/047,463, Response filed May 21, 2020 to Non Final Office Action mailed Feb. 21, 2020", 18 pgs.
"U.S. Appl. No. 16/047,463, Response filed Oct. 28, 2020 to Final Office Action mailed Sep. 4, 2020", 12 pgs.
"U.S. Appl. No. 16/156,728, Final Office Action mailed Jan. 31, 2022", 19 pages.
"U.S. Appl. No. 16/156,728, Non Final Office Action mailed Jul. 7, 2021", 19 pages.
"U.S. Appl. No. 16/156,728, Non Final Office Action mailed Dec. 23, 2020", 22 pgs.
"U.S. Appl. No. 16/156,728, Response filed Mar. 18, 2021 to Non Final Office Action mailed Dec. 23, 2020", 17 pgs.
"U.S. Appl. No. 16/156,728, Response filed Oct. 6, 2021 to Non Final Office Action mailed Jul. 7, 2021", 16 pgs.
"U.S. Appl. No. 16/156,728, Response filed Oct. 12, 2020 to Restriction Requirement mailed Aug. 21, 2020", 9 pgs.
"U.S. Appl. No. 16/156,728, Restriction Requirement mailed Aug. 21, 2020", 7 pgs.
"U.S. Appl. No. 16/156,747, Corrected Notice of Allowability mailed May 18, 2021", 2 pgs.
"U.S. Appl. No. 16/156,747, Corrected Notice of Allowability mailed Sep. 15, 2021", 4 pgs.
"U.S. Appl. No. 16/156,747, Non Final Office Action mailed Oct. 21, 2020", 9 pgs.
"U.S. Appl. No. 16/156,747, Notice of Allowance mailed Apr. 26, 2021", 5 pgs.
"U.S. Appl. No. 16/156,747, Response filed Jan. 20, 2021 to Non Final Office Action mailed Oct. 21, 2020", 13 pgs.
"U.S. Appl. No. 16/156,747, Response filed Jul. 27, 2020 to Restriction Requirement mailed Jun. 5, 2020", 7 pgs.

(56) References Cited

OTHER PUBLICATIONS

"U.S. Appl. No. 16/156,747, Restriction Requirement mailed Jun. 5, 2020", 8 pgs.
"U.S. Appl. No. 16/652,896, Notice of Allowance mailed Jan. 28, 2022", 7 pgs.
"U.S. Appl. No. 16/652,896, Preliminary Amendment Filed Apr. 1, 2020", 8 pgs.
"U.S. Appl. No. 16/652,896, Supplemental Notice of Allowability mailed Feb. 9, 2022", 2 pgs.
"U.S. Appl. No. 17/385,385, Preliminary Amendment filed Aug. 18, 2021", 7 pgs.
"Australian Application Serial No. 2018347354, First Examination Report mailed Dec. 14, 2020", 6 pgs.
"Australian Application Serial No. 2018347354, Response filed Jan. 29, 2021 to First Examination Report mailed Dec. 14, 2020", 29 pgs.
"Australian Application Serial No. 2018347354, Response filed Apr. 16, 2021 to Subsequent Examiners Report mailed Feb. 11, 2021", 18 pgs.
"Australian Application Serial No. 2018347354, Subsequent Examiners Report mailed Feb. 11, 2021", 5 pgs.
"Australian Application Serial No. 2021209337, First Examination Report mailed Aug. 9, 2021", 4 pgs.
"Australian Application Serial No. 2021209337, Response filed Oct. 12, 2021 to First Examination Report mailed Aug. 9, 2021", 8 pgs.
"Australian Application Serial No. 2021209337, Response filed Oct. 15, 2021 to Subsequent Examiners Report mailed Oct. 14, 2021", 6 pgs.
"Australian Application Serial No. 2021209337, Subsequent Examiners Report mailed Oct. 14, 2021", 3 pgs.
"Canadian Application Serial No. 3,078,736, Office Action Mailed Feb. 1, 2022", 5 pages.
"Canadian Application Serial No. 3,078,736, Office Action mailed Apr. 29, 2021", 5 pages.
"Canadian Application Serial No. 3,078,736, Response filed Aug. 26, 2021 to Office Action mailed Apr. 29, 2021", 18 pgs.
"Chinese Application Serial No. 201880066636.2, Office Action mailed May 31, 2021", with English translation, 14 pages.
"Chinese Application Serial No. 201880066636.2, Response filed Sep. 13, 2021 to Office Action mailed May 31, 2021", with English claims, 14 pages.
"European Application Serial No. 18796230.3, Communication Pursuant to Article 94(3) EPC mailed Apr. 22, 2021", 4 pgs.
"European Application Serial No. 18796230.3, Response filed Nov. 2, 2021 to Communication Pursuant to Article 94(3) EPC mailed Apr. 22, 2021", 20 pgs.
"European Application Serial No. 18796230.3, Response to Communication pursuant to Rules 161(1) and 162 EPC filed Nov. 30, 2020", 22 pgs.
"European Application Serial No. 18797274.0, Response to Communication pursuant to Rules 161(1) and 162 EPC filed Dec. 9, 2020", 18 pgs.
"International Application Serial No. PCT/US2018/055218, International Preliminary Report on Patentability mailed Apr. 23, 2020", 7 pgs.
"International Application Serial No. PCT/US2018/055218, International Search Report mailed Jan. 30, 2019", 5 pgs.
"International Application Serial No. PCT/US2018/055218, Written Opinion mailed Jan. 30, 2019", 5 pgs.
"International Application Serial No. PCT/US2018/055232, International Preliminary Report on Patentability mailed Apr. 23, 2020", 12 pgs.
"International Application Serial No. PCT/US2018/055232, International Search Report mailed Mar. 19, 2019", 8 pgs.
"International Application Serial No. PCT/US2018/055232, Invitation to Pay Additional Fees and Partial Search Report mailed Jan. 24, 2019", 14 pgs.
"International Application Serial No. PCT/US2018/055232, Written opinion mailed Mar. 19, 2019", 12 pgs.
"Japanese Application Serial No. 2020-520521, Final Notification of Reasons for Refusal mailed Feb. 22, 2022", with English translation, 5 pages.
"Japanese Application Serial No. 2020-520521, Final Notification of Reasons for Refusal mailed Nov. 2, 2021", with English translation, 4 pages.
"Japanese Application Serial No. 2020-520521, Notification of Reasons for Refusal mailed May 25, 2021", with English translation, 9 pages.
"Japanese Application Serial No. 2020-520521, Response filed Jan. 13, 2022 to Final Notification of Reasons for Refusal mailed Nov. 2, 2021", with English claims, 17 pages.
"Japanese Application Serial No. 2020-520521, Response filed Aug. 12, 2021 to Notification of Reasons for Refusal mailed May 25, 2021", with English claims, 21 pages.
"Smith & Nephew", Legion Cones Surgical Technique V1, (Jan. 2017), 36 pgs.
"U.S. Appl. No. 16/652,896, Supplemental Notice of Allowability mailed May 11, 2022", 2 pgs.
"Japanese Application Serial No. 2020-520521, Response filed Apr. 27, 2022 to Final Notification of Reasons for Refusal mailed Feb. 22, 2022", with English claims, 11 pages.
"Canadian Application Serial No. 3,078,736, Response filed Jun. 1, 2022 to Office Action Mailed Feb. 1, 2022", 23 pgs.
"Australia Application Serial No. 2022200138, First Examination Report mailed Sep. 23, 2022", 3 pgs.
U.S. Appl. No. 16/156,728, filed Oct. 10, 2018, Revision Knee Arthroplasty Methods and Instruments.
U.S. Appl. No. 16/156,747 now U.S. Pat. No. 11,141,290, filed Oct. 10, 2018, Revision Knee Arthroplasty Methods and Instruments.
U.S. Appl. No. 17/385,385, filed Jul. 26, 2021, Revision Knee Arthroplasty Methods and Instruments.
U.S. Appl. No. 16/047,463 now U.S. Pat. No. 10,987,225, filed Jul. 27, 2018, Systems and Methods for Attaching Sleeve or Cone in Prosthetic Implant Having a Stem.
U.S. Appl. No. 16/652,896, filed Apr. 1, 2020, Implantation Cradle.
"Chinese Application Serial No. 202210322683.7, Response Filed Jul. 1, 2025 to Office Action mailed Mar. 13, 2025", W/ English Claims, 17 pgs.
"Australia Application Serial No. 2022200138, Response filed Nov. 15, 2022 First Examination Report mailed Sep. 23, 2022", 10 pgs.
"Australia Application Serial No. 2022200138, Subsequent Examiners Report mailed Dec. 1, 2022", 3 pgs.
"Australia Application Serial No. 2022200138, Response filed Jan. 31, 2023 to Subsequent Examiners Report mailed Dec. 1, 2022", 9 pgs.
"Japanese Application Serial No. 2022-125533, Notification of Reasons for Refusal mailed May 9, 2023", w English Translation, 8 pgs.
"Japanese Application Serial No. 2022-125533, Response filed Aug. 7, 2023 to Notification of Reasons for Refusal mailed May 9, 2023", w English claims, 20 pgs.
"European Application Serial No. 22208169.7, Extended European Search Report mailed Oct. 4, 2023", 7 pgs.
"Japanese Application Serial No. 2022-125533, Final Notification of Reasons for Rejection mailed Sep. 26, 2023", W English Translation, 6 pgs.
"Japanese Application Serial No. 2022-125533, Response Filed Dec. 13, 2023 to Final Notification of Reasons for Rejection mailed Sep. 26, 2023", w English Claims, 11 pgs.
"European Application Serial No. 22208169.7, Response filed Apr. 29, 2024 to Extended European Search Report mailed Oct. 4, 2023", 31 pgs.
"Australian Application Serial No. 2023202761, First Examination Report mailed May 31, 2024", 4 pgs.
"Australian Application Serial No. 2023202761, Response filed Aug. 9, 2024 to First Examination Report mailed May 31, 2024", 9 pgs.
"Australian Application Serial No. 2023202761, Subsequent Examination Report mailed Sep. 4, 2024", 3 pgs.
"U.S. Appl. No. 17/385,385, Restriction Requirement mailed Oct. 9, 2024", 6 pgs.

(56) References Cited

OTHER PUBLICATIONS

"Australian Application Serial No. 2023202761, Response filed Oct. 14, 2024 to Subsequent Examination Report mailed Sep. 4, 2024", 12 pgs.
"U.S. Appl. No. 17/385,385, Response filed Dec. 5, 2024 to Restriction Requirement mailed Oct. 9, 2024", 6 pgs.
"Canadian Application Serial No. 3,207,198, Examiners Rule 86(2) Requisition mailed Dec. 2, 2024", 4 pgs.
"U.S. Appl. No. 17/385,385, Non Final Office Action mailed Feb. 12, 2025", 20 pgs.
"Japanese Application Serial No. 2024-032855, Notification of Reasons for Rejection mailed Jan. 21, 2025", W English Translation, 8 pgs.
"Canadian Application Serial No. 3,207,198, Response filed Mar. 4, 2025 to Examiners Rule 86(2) Requisition mailed Dec. 2, 2024", 13 pgs.
"Japanese Application Serial No. 2024-032855, Response filed Apr. 10, 2025 to Notification of Reasons for Rejection mailed Jan. 21, 2025", W English Claims, 12 pgs.
"Chinese Application Serial No. 202210322683.7, Office Action mailed Mar. 13, 2025", W English Translation, 14 pgs.
"U.S. Appl. No. 17/385,385, Response filed May 12, 2025 to Non Final Office Action mailed Feb. 12, 2025", 16 pgs.
"U.S. Appl. No. 17/385,385, Final Office Action mailed Aug. 19, 2025", 19 pgs.
"U.S. Appl. No. 17/385,385, Examiner Interview Summary mailed Oct. 24, 2025", 3 pgs.
"Australian Application Serial No. 2025200297, First Examination Report mailed Dec. 9, 2025", 6 pgs.
"Chinese Application Serial No. 202210322683.7, Office Action mailed Oct. 20, 2025", w/English translation, 9 pgs.
"Canadian Application Serial No. 3,207,198, Examiners Rule 86(2) Report mailed Feb. 6, 2026", 4 pgs.
"Australian Application Serial No. 2025200297, Response filed Feb. 16, 2026 to First Examination Report mailed Dec. 9, 2025", W English Claims, 19 pgs.
"Chinese Application Serial No. 202210322683.7, Response Filed Dec. 17, 2025 to Office Action mailed Oct. 20, 2025", w/English Claims, 14 pgs.
"Chinese Application Serial No. 202210322683.7, Response to Examiner Telephone Interview Filed Mar. 16, 2026", w/English Claims, 5 pgs.
"Australian Application Serial No. 2025200297, Subsequent Examination Report mailed Mar. 23, 2026", 4 pgs.
"European Application Serial No. 26156130.2, Extended European Search Report mailed Apr. 9, 2026", 8 pgs.

* cited by examiner

IMPACTION CRADLE

CLAIM OF PRIORITY

This application claims the benefit of U.S. Provisional Patent Application Ser. No. 62/570,889, filed on Oct. 11, 2017, the benefit of priority of which is claimed hereby, and which is incorporated by reference herein in its entirety.

TECHNICAL FIELD

This document pertains generally, but not by way of limitation, to a cradle for supporting implants for knee arthroplasty procedures during attachment of intramedullary components, such as stems or sleeves, to the implants.

BACKGROUND

Knee joints are formed by resting femoral condyles of the femur on articulating surfaces of the tibia. In knee arthroplasty procedures, at least one of the femoral condyles can be at least partially resected and replaced with a femoral component having articulating surfaces oriented and shaped approximate the natural condyles. The medial condyle of the femur is typically larger than the lateral condyle as the medial condyle is closer to the sagittal plane thereby supporting more of the body weight. Similarly, corresponding condyles of the tibia can be similarly resected and replaced with tibial implants having articulating surfaces approximating the natural articulating surfaces.

Intramedullary sterns or metaphyseal sleeves may be attached to the femoral or tibial implant opposite the articulating surfaces in order to provide additional fixation. The opposite end of the intramedullary stem can then be driven into the intramedullary canal of the femur or tibia to provide additional fixation of the implant to the corresponding bone. The relative angle of the intramedullary stem to the articulating surfaces is a primary concern as the articulating surfaces must be properly oriented to correctly engage the corresponding articulating surfaces of the opposing implant and restore the knee joint kinematics to simulate those of a natural knee joint. In a standing person, the mechanical axis is defined as extending between the center of the femoral head and the center of the ankle joint. The mechanical axis is commonly offset from the vertical axis by about 3° depending on the height and hip width of the individual. The anatomical axis is defined as the axis coaxial to the intramedullary canal of either the femur or the tibia, which is typically 5° to 7° offset from the mechanical axis of the bone. In addition, an individual's natural joint line can be further angled at a slight varus or valgus angle (about 2° to 3°) from the mechanical axes of the femur and tibia due to the sizing and shape of the individual's condyles and femur and tibia.

Due to the irregular shape of the articulating surfaces of the femoral and tibial implant, attaching an intramedullary stem or metaphyseal sleeve to the implant along the correct axis can be challenging. In addition, as the intramedullary stem is commonly driven into the implant mount through impaction, surgeons must accurately strike the intramedullary stem and avoid knocking the intramedullary stem out of alignment.

Overview

The present inventors have recognized, among other things, that a problem to be solved can include accurately impacting intramedullary stems or metaphyseal sleeves into engagement with femoral or tibial implants due to the varus-valgus angulation of the femoral or tibial implants. In an example, the present subject matter can provide a solution to this problem, such as by providing an impaction cradle for supporting the femoral or tibial implant on a planar support surface (e.g. a tabletop). The impaction cradle can be configured to account for the varus-valgus angulation of the femoral or tibial implant such that the attachment feature of the implant is oriented within a vertical plane or towards the true vertical axis. In this orientation, the intramedullary stem or metaphyseal sleeve can be impacted along a generally vertical axis or plane relative to the support surface to drive the intramedullary stem into the attachment feature. The generally vertical impaction angle can be easier for medical practitioners to accurately impact the intramedullary stem or metaphyseal sleeve, which lowers the risk of damage to the intramedullary stem, metaphyseal sleeve, or the femoral or tibial implant.

This overview is intended to provide an overview of subject matter of the present patent application. It is not intended to provide an exclusive or exhaustive explanation of the present subject matter. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
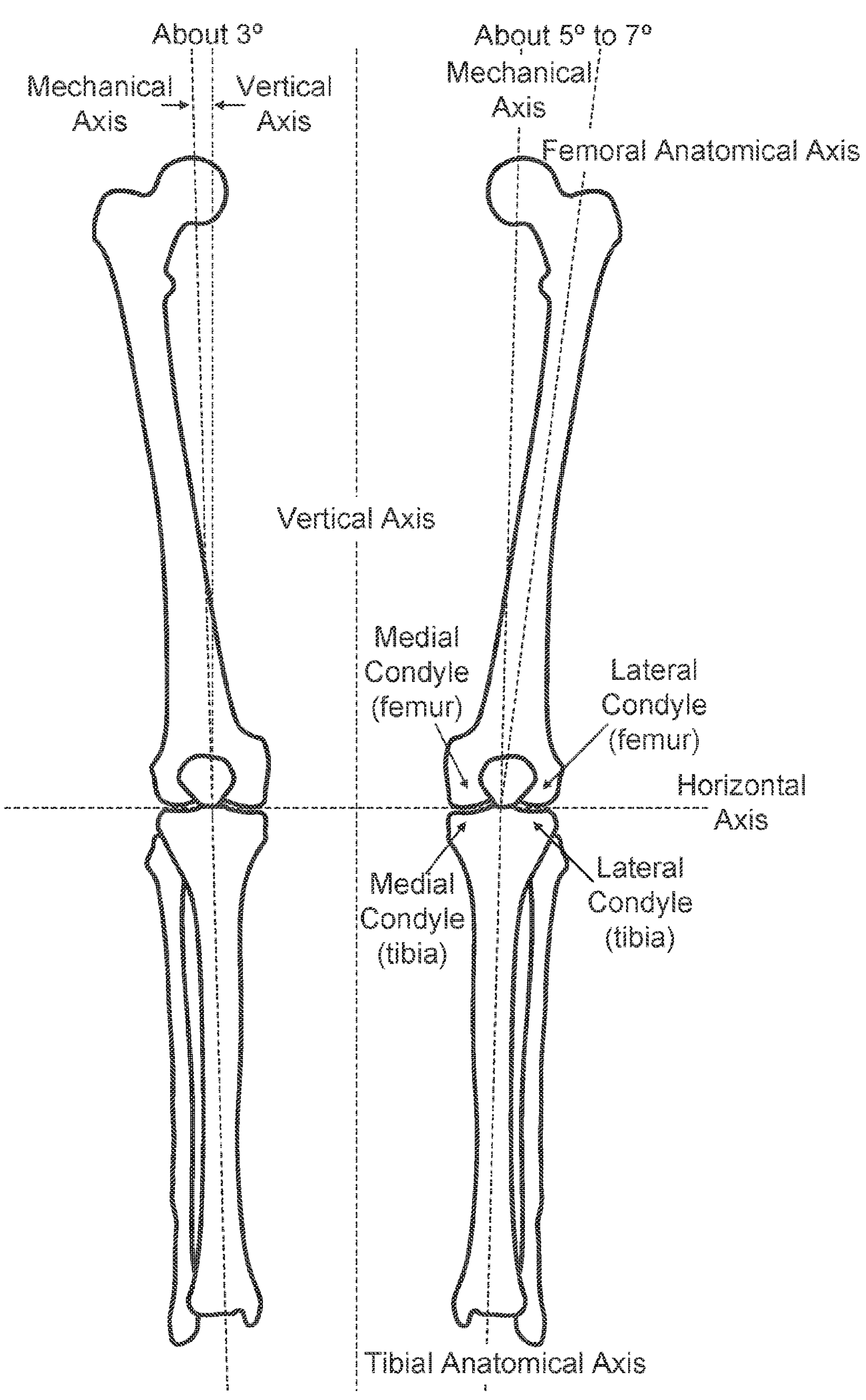
FIG. 1 is a schematic view of a representative skeletal structure of the legs of a standing person.

As illustrated in FIG. 1, in a standing person, the lateral and medial condyles of the femur rest on a meniscus positioned on the lateral and medial condyles of the tibia. As the hips of most people are often wider than their knees and ankles, their legs are often pivoted slightly inward toward the sagittal plane when standing. For the purposes of this disclosure, the mechanical axis can be defined as an axis drawn from the femoral head to the center of the ankle joint such that the axis passes through the knee slightly media to the tibial spine. The mechanical axis can subtend about 3° to the true vertical axis when the person is standing depending on the height of the person and/or the width of their pelvis.

In a standing person, the articulating surfaces of the lateral and medial condyles of the tibia are positioned in a plane parallel to the true horizontal axis. The tibial anatomical axis can be defined as an axis extending along the length of the intramedullary canal of the tibia. The tibial anatomical axis can be generally parallel to the mechanical axis. The femoral anatomical axis can be defined as the axis extending along the intramedullary canal of the femur. As discussed above, the femoral anatomical axis is typically offset about 5° to 7° from the mechanical axis (about 8° to 10° from the true vertical axis). In addition, an individual's natural joint line can be further angled at a slight varus or valgus angle (about 2° to 3°) from the mechanical axes of the femur and tibia due to the sizing and shape of the individual's condyles and femur and tibia. The overall varus or valgus angle can be defined as the angle from the vertical axis created by the offset of femoral anatomical axis and the varus and valgus variations caused by the sizing and shape of the individual's bone structures.

As depicted in FIGS. 4-6B, a femoral component 10, according to an example of the present disclosure, can comprise a medial condyle portion 14 and a lateral condyle portion 12. Each condyle portion 12, 14 can have an articulating surface 16 and an inner bone contacting surface 18. The lateral condyle portion 12 can be shaped and sized to approximate the natural lateral condyle of the femur and the medial condyle portion 14 can be shaped and sized to approximate the natural medial condyle of the femur. In particular, the medial condyle portion 12 can be larger in size than the lateral condyle portion 14 to correspond to the relative sizing of natural femoral condyles. The lower most portion of articulating surface 16 of the condyle portions 12, 14 can define an articulating plane generally corresponding to the natural horizontal plane defined by the tibial condyles of a standing person.

In an embodiment, the medial condyle portion 14 and the lateral condyle portion 12 can be connected at one end by the femoral cam 20 and at the opposite end by the patellofemoral flange 22. In this configuration, a gap 24 can be defined between the medial condyle portion 14 and the lateral condyle portion 12. The gap 24 corresponding to the natural gap between the medial and lateral condyles of the distal femoral component.

Figure 5A:
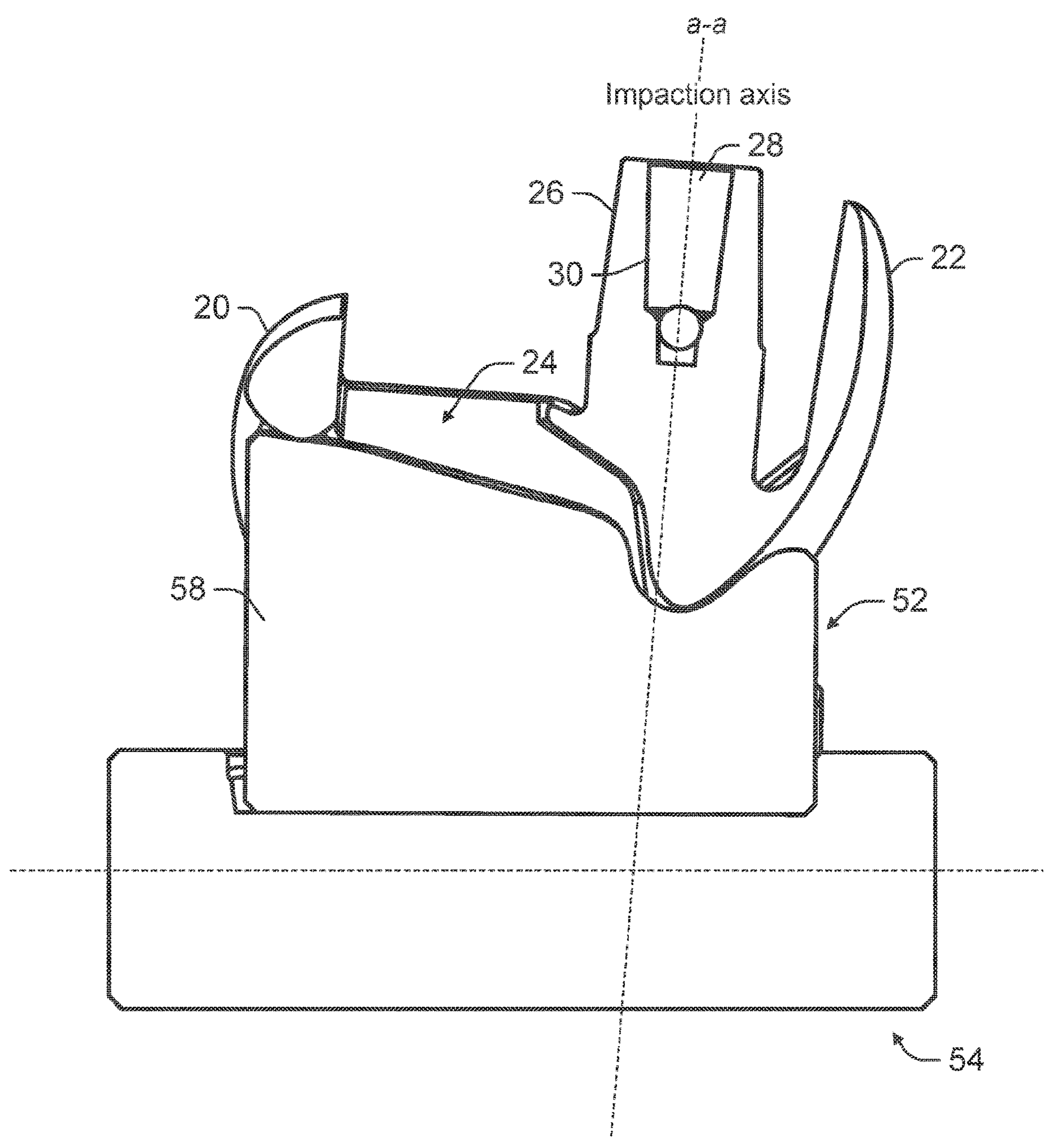
FIG. 5A is a side cross-sectional view of the impaction cradle with the femoral implant depicted in FIG. 4.
Figure 5B:
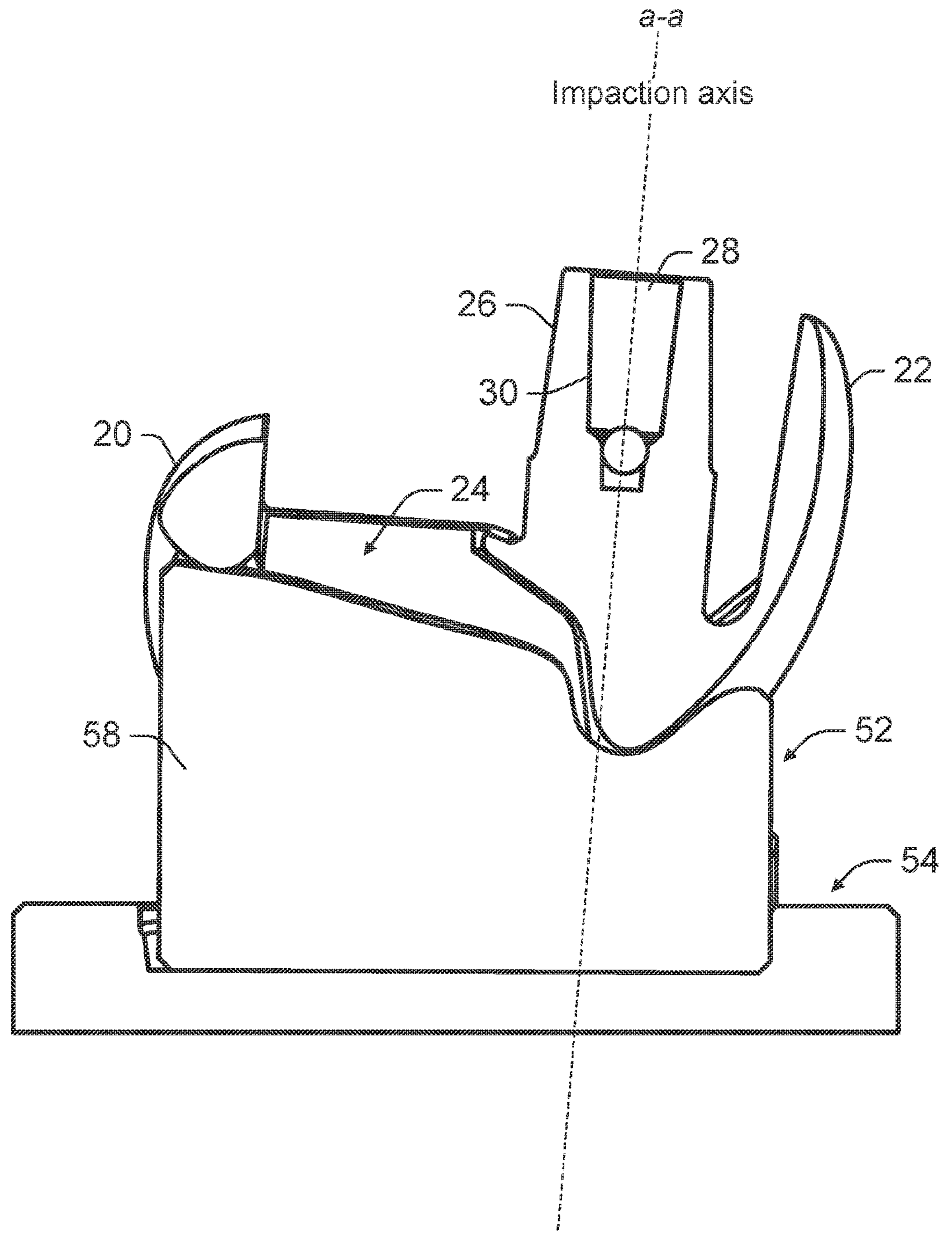
FIG. 5B is a partial side cross-sectional view of the impaction cradle with the femoral implant depicted in FIG. 5B.
Figure 6A:
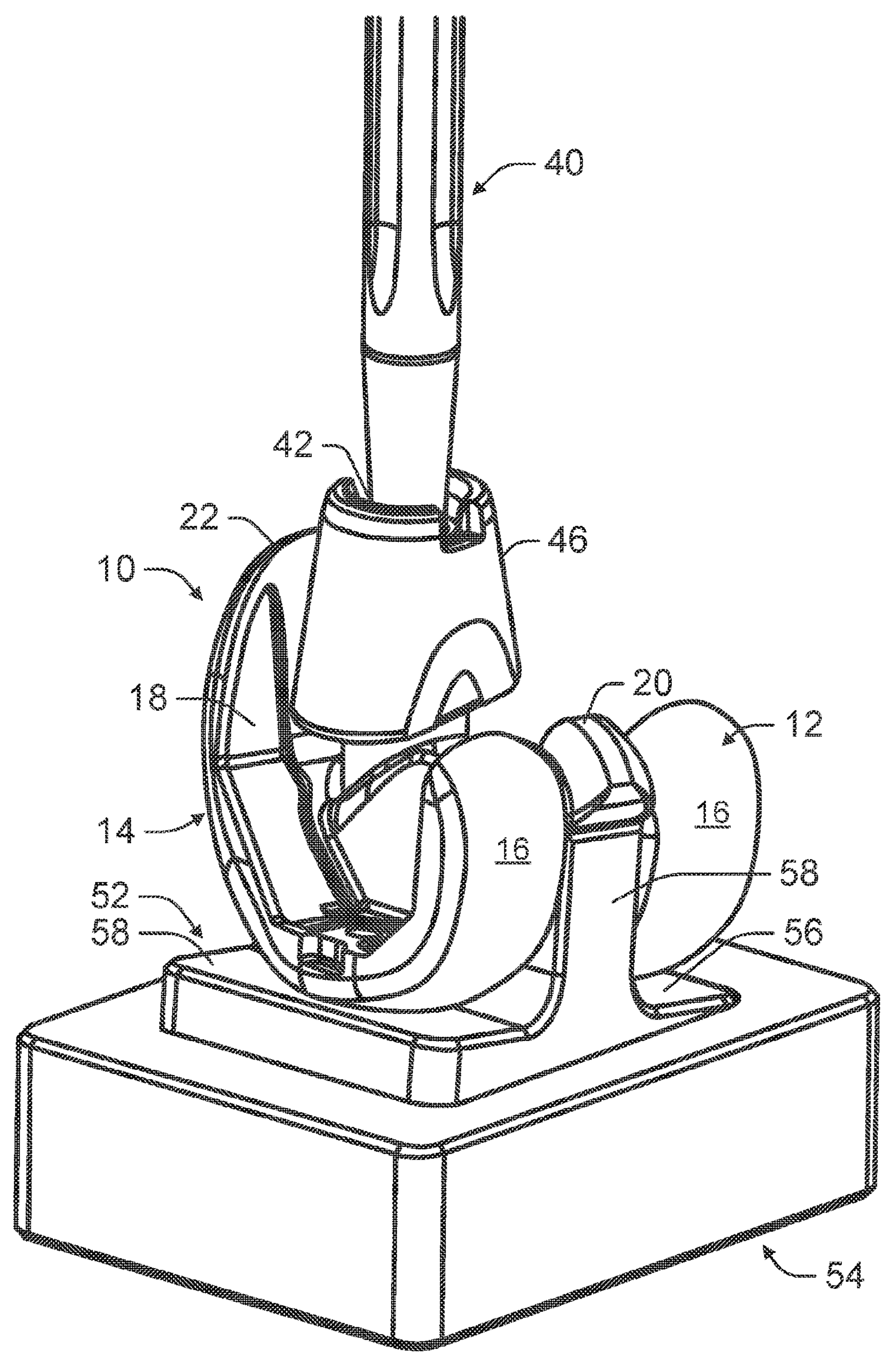
FIG. 6A is a perspective view an impaction cradle with a femoral implant resting thereon, wherein an intramedullary stem and metaphyseal sleeve are impacted onto the femoral implant according to an example of the present disclosure.
Figure 6B:
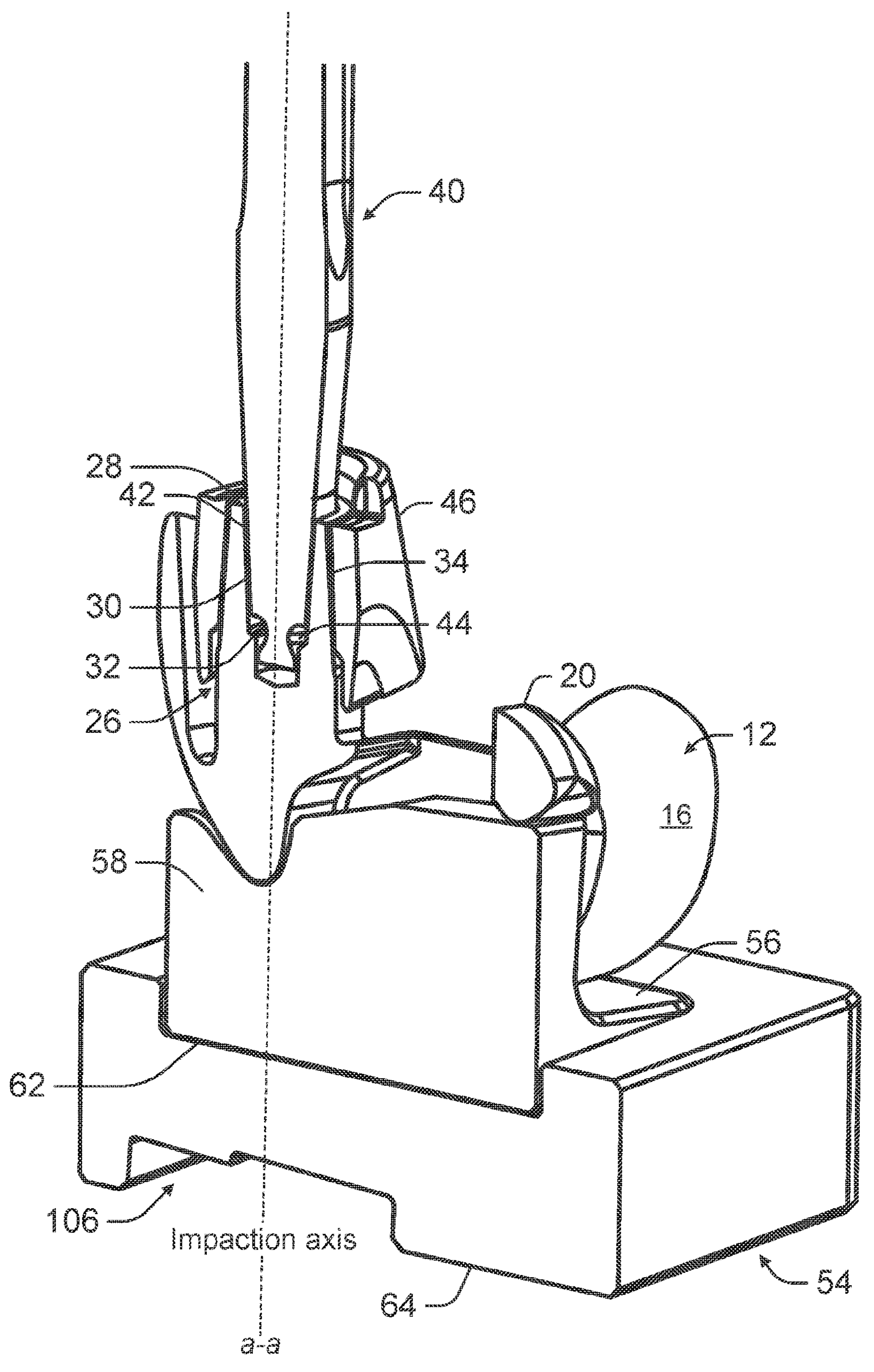
FIG. 6B is a cross-sectional perspective view the impaction cradle with the femoral implant and impacted intramedullary stern and metaphyseal sleeve depicted in FIG. 6A.
Figure 7:
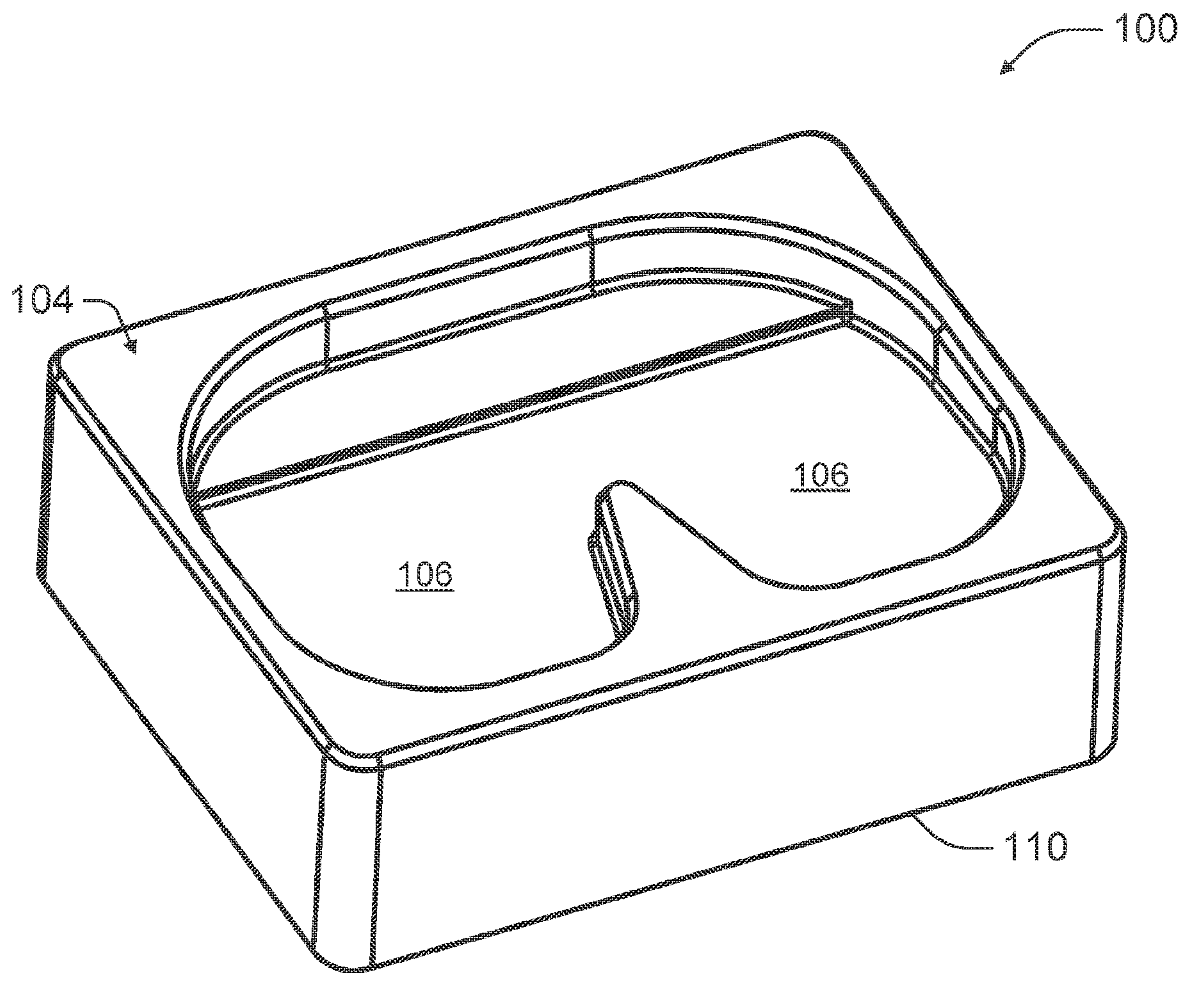
FIG. 7 is a perspective view of an impaction cradle for a tibia implant according to an example of the present disclosure.
Figure 8:
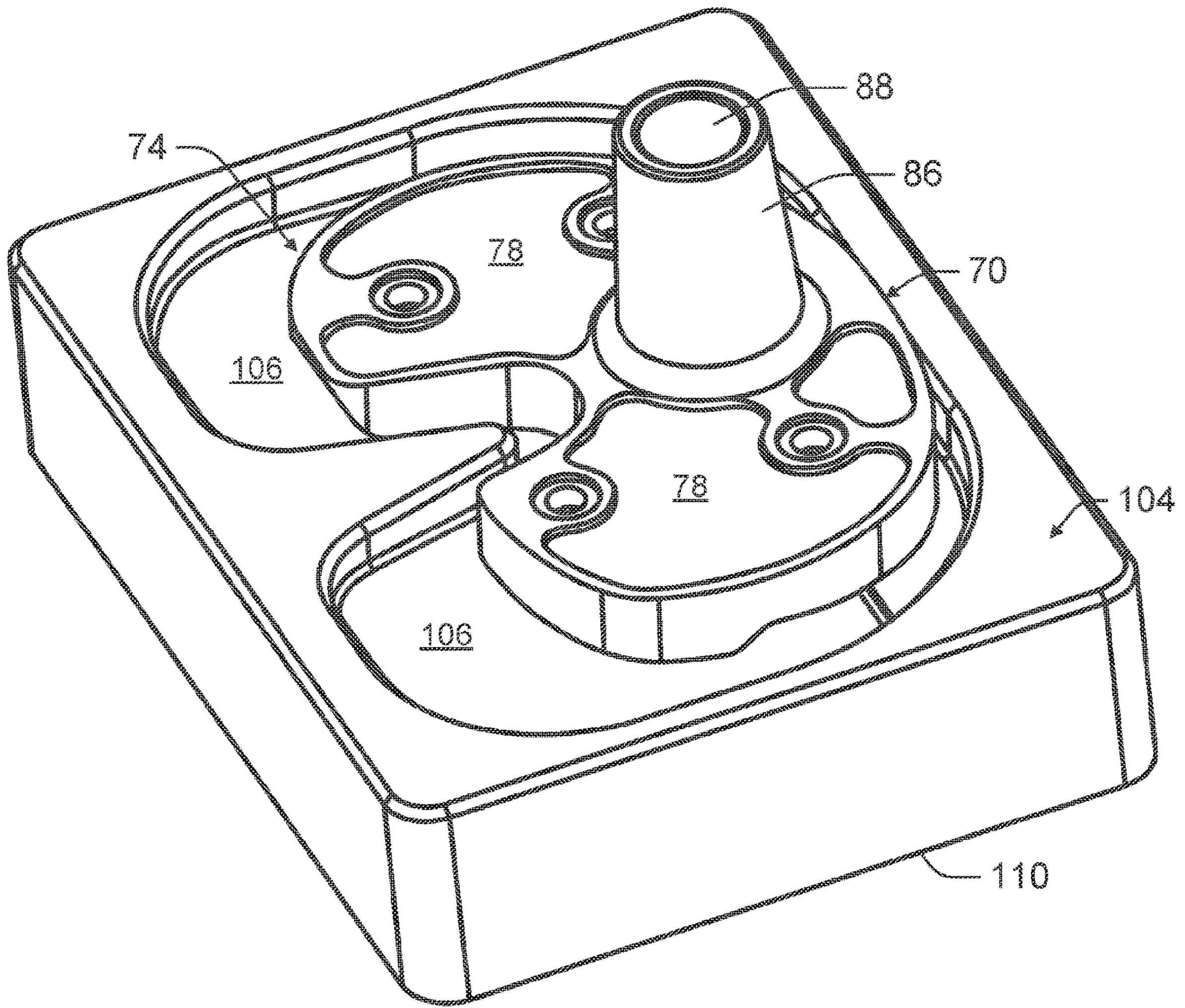
FIG. 8 is a perspective view of an impaction cradle with a tibia implant resting thereon according to an example of the present disclosure.

As depicted in FIGS. 5A-B and 6A-B, in an embodiment, the femoral component 10 comprises an attachment feature 26 positioned on the bone engaging surface in the middle of the femoral component where the two condyles 16 meet the patellofemoral flange 22. As depicted in FIG. 5B, the attachment feature 26 can comprise an attachment port 28 defining an inner surface 30 for engaging an attachment end 42 of an intramedullary stem 40. In an embodiment, the inner surface 30 and the attachment end 42 can have corresponding Morse tapers such that the inner surface 30 frictionally engages the attachment end 42 as the intramedullary stem 40 is impacted into the attachment port 28 along an impaction axis a-a. As depicted in FIG. 5A, the impaction axis a-a can be angled offset from a perpendicular angle to the support plane. In at least one example, the impaction axis a-a can be oriented at an angle perpendicular to the support plane. As depicted in FIG. 6B, in an embodiment, the attachment end 42 of the intramedullary stern 40 can comprise a notched portion 44. In this configuration, the attachment feature 26 can comprise a detent feature 32 positioned to engage the notched portion 44 to lock the intramedullary stem 40 to the femoral implant 10. The detent feature 32 can be positioned at the bottom of the attachment port 28 to engage the notched portion 44 when the intramedullary stem 40 is fully impacted into the attachment port 28 of the femoral implant 10.

When the femoral component rests on the condyle surfaces 16 which are perpendicular to the mechanical axis of the bone, the attachment feature 26 and attachment port 28 can be angled such that the impaction axis a-a is angled relative to the articulating surface. The angle of the impaction axis a-a can simulate the natural subtend of the femoral anatomical axis from the mechanical axis (about 5° to about 7° and, in certain embodiments, about 6°). In an embodiment, a plurality of femoral components 10 can be provided to a medical practitioner, wherein each femoral component 10 can have an attachment port 28 oriented at a different angle to the articulating plane. In this configuration, the medical practitioner can select the appropriate femoral component 10 to corresponding to the particular subtend of the femoral anatomical axis of the particular patient.

As depicted in FIGS. 6A-B, in an embodiment, the femoral implant component 10 can include a sleeve or cone 46 positioned over an outer surface 34 of the attachment feature 26. The sleeve 46 can comprise a porous material, such as titanium, tantalum, or alloys thereof, for facilitating bone ingrowth and fixation of the femoral implant component 10.

As depicted in FIGS. 2-6B, an impaction cradle 50, according to an example of the present disclosure, can comprise a cradle element 52 and a base portion 54. The cradle element 52 can be configured to receive and support the femoral implant 10. The base portion 54 can rest on a planar support surface (e.g. table top) to support the cradle element 52 and femoral implant 10 thereon. The cradle element 52 and/or the base portion 54 can orient a femoral implant 10 resting on the cradle element 52 such that impaction axis a-a defined by the attachment port 28 is oriented vertically. In an embodiment, the femoral implant 10 can be oriented such that the impaction axis a-a is within a vertical plane bisecting the femoral implant 10 between the medial condyle portion 14 and the lateral condyle portion 12. In this configuration, the femoral implant 10 can be angled transverse to the vertical axis and oriented slightly forward or backwards but within the vertical plane.

As depicted in FIGS. 2-6B, in an embodiment, the cradle element 52 can include at least one support surface 56 shaped to interface with a corresponding surface of the femoral implant 10. The support surface 56 can be shaped to interface with an articulating surface 16 of the medial condyle portion 14 or the lateral condyle portion 12 or another surface of the femoral implant 10. In an embodiment, the cradle element 52 can include at least two support surface 56, wherein one support surface 56 corresponds to the medial condyle portion 14 and another support surface 56 corresponds to the lateral condyle portion 12. The support surface 56 can define a support plane parallel to the articulating plane defined by medial condyle portion 14 and the lateral condyle portion 12 when the femoral implant 10 is positioned on the cradle element 52.

Figure 2:
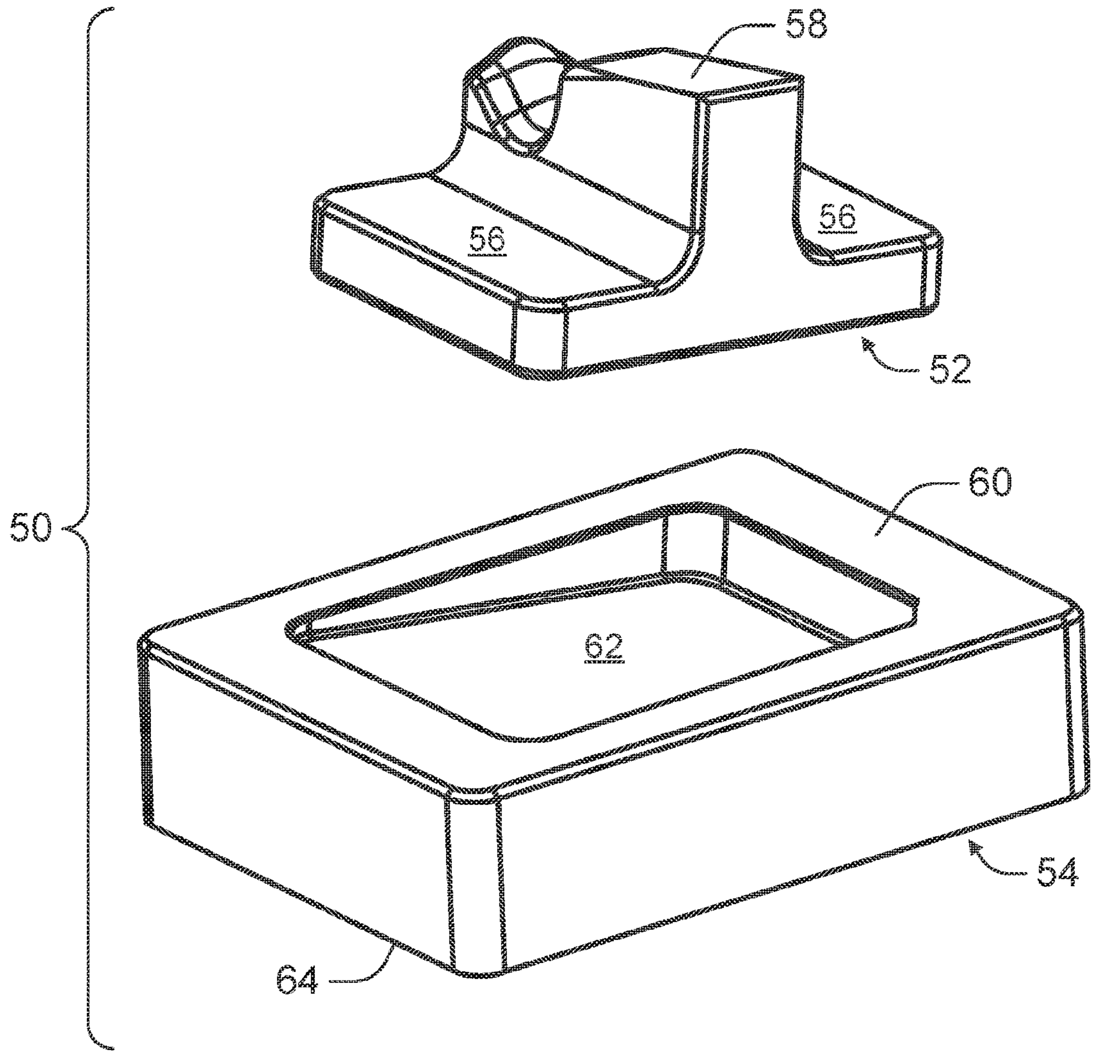
FIG. 2 is a perspective exploded view of an impaction cradle for a femoral implant according to an example of the present disclosure.
Figure 3:
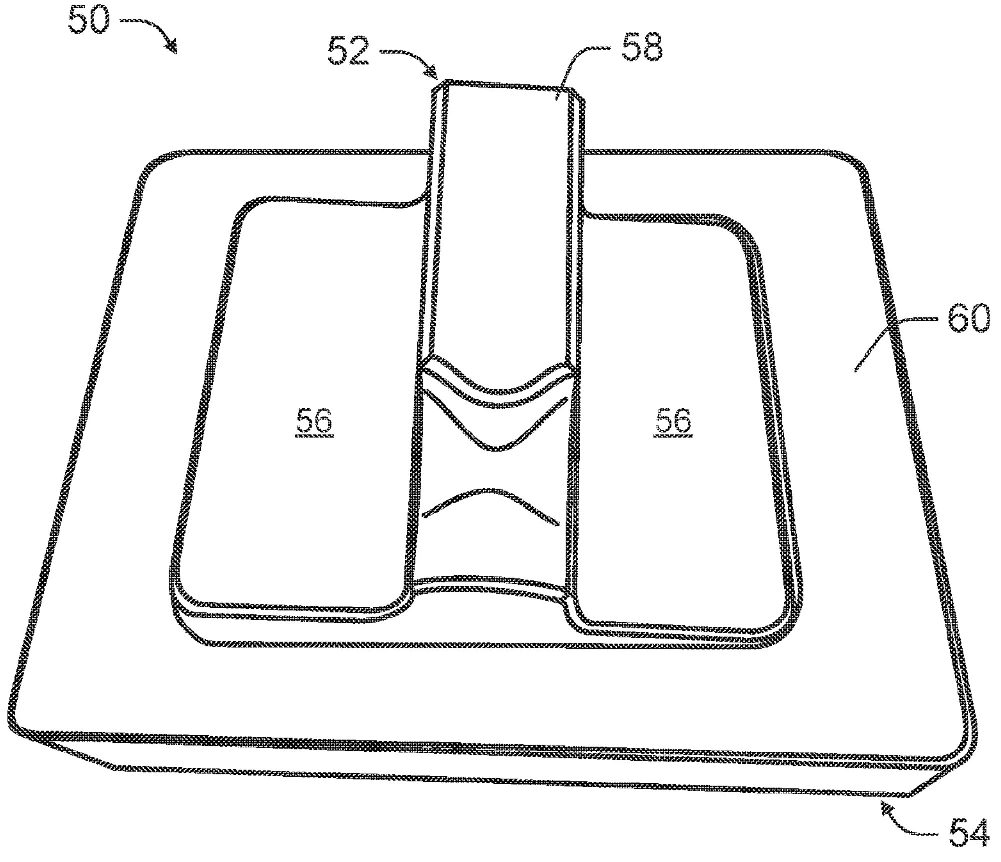
FIG. 3 is a top perspective view of an impaction cradle for a femoral implant according to an example of the present disclosure.
Figure 4:
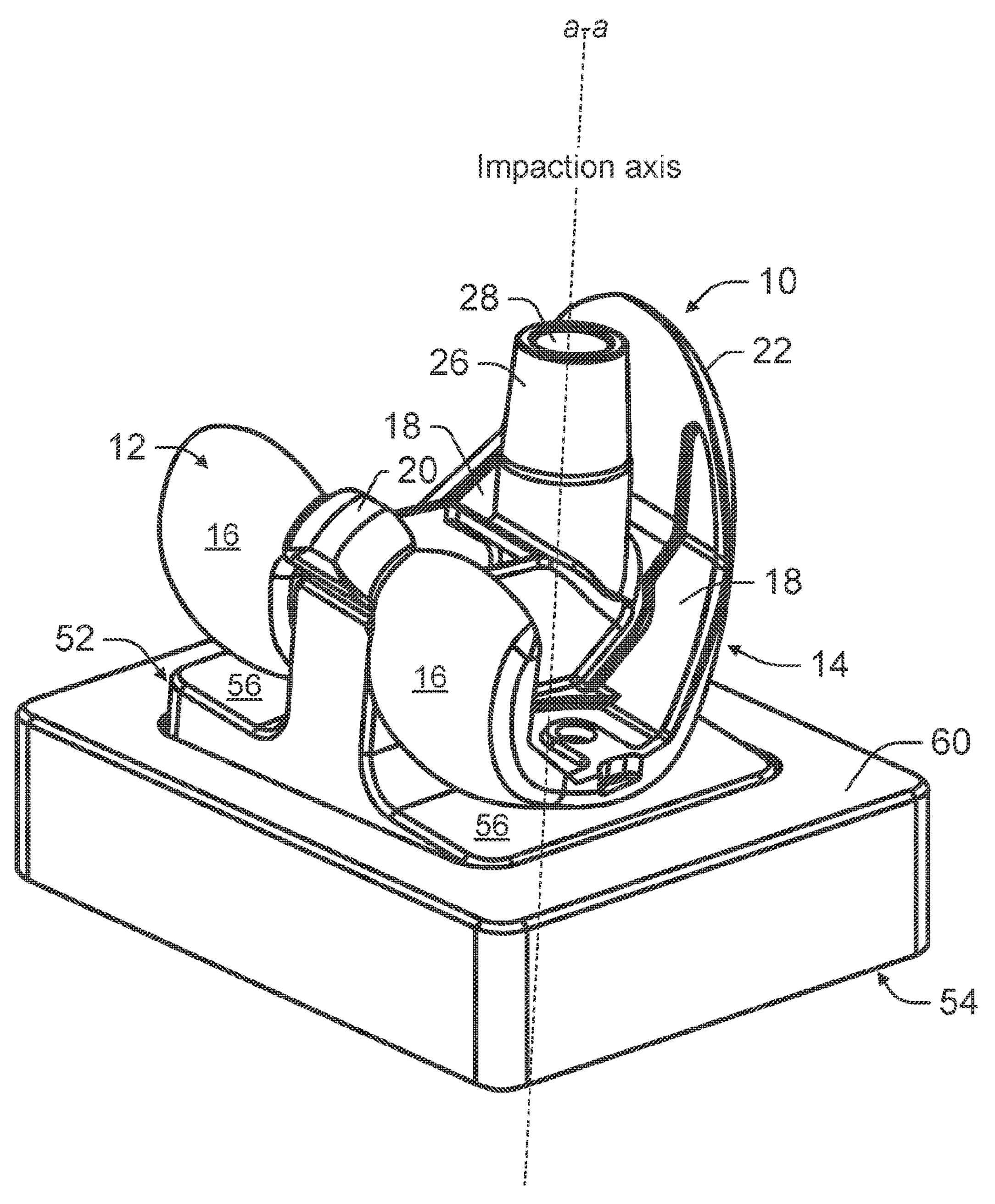
FIG. 4 is a perspective view of an impaction cradle with a femoral implant resting thereon according to an example of the present disclosure.

As depicted in FIGS. 2-4, in an embodiment, the cradle element 52 can comprise a stabilizing post 58 positioned between two support surfaces 56 corresponding to the medial condyle portion 14 and the lateral condyle portion 12. The stabilizing post 58 can extend above the support surfaces 56 such that the stabilizing post 58 can be received within the gap 24 between the medial condyle portion 14 and the lateral condyle portion 12. The stabilizing post 58 can engage the medial condyle portion 14 and the lateral condyle portion 12 to maintain the femoral implant 10 on the cradle element 52.

As illustrated in FIGS. 2-6B, in an embodiment, the base portion 54 can comprise a planar body 60 defining a base plane. The base portion 54 can orient the cradle element 52 such that the support plane defined by the support surfaces 56 are oriented at an angle to the base plane corresponding to the varus-valgus angle. In an embodiment, the varus-valgus angle of the support plane to the base plane is about 8° to 10° to correspond to the natural subtend of the femoral anatomical axis to the mechanical axis. In this configuration, a femoral implant 10 positioned on the cradle element 52 oriented such that the impaction axis a-a is parallel to a vertical axis or within a vertical plane bisecting the femoral implant 10 between the medial condyle portion 14 and the lateral condyle portion 12. The generally vertical orientation of the impaction axis a-a can reduce the difficulty of accurately impacting an intramedullary stem 40 into the attachment feature 26.

As depicted in FIGS. 1 and 5A-B, in an embodiment, the planar body 60 of the base portion 54 can comprise an angled upper surface 62 for receiving the cradle element 52. The angled upper surface 62 can be angled at the varus-valgus angle to orient the support plane of the cradle element 52 transverse to the base plane at the varus-valgus angle. In an embodiment, the planar body 60 can comprise a planer lower surface 64 for position the base portion 54 on a planar support surface (e.g. a table or work bench). The planer lower surface 64 can be parallel to the base plane such that resting the planar lower surface 64 on a planar surface orients the support surface of the cradle element 52 at an angle to the base plane and planar support surface corresponding to the varus-valgus angle. The orientation of the support surfaces at the varus-valgus angle orients a femoral implant 10 received on the support surfaces such that the impaction axis a-a is oriented vertically or nearly vertical to allow for easier and more accurate impactions of the intramedullary stem.

As depicted in FIGS. 8-10B, a tibial implant 70, according to an example of the present disclosure, can comprise a medial condyle portion 72 and a lateral condyle portion 74. Each condyle portion 72, 74 can have an articulating surface 76 and an inner bone contacting surface 78. The lateral condyle portion 74 can be shaped and sized to approximate the natural lateral condyle of the tibia and the medial condyle portion 72 can be shaped and sized to approximate the natural medial condyle of the tibia. In particular, the lateral condyle portion 74 can have a larger size to provide a larger articulating surface 76 for the larger femoral lateral condyle. The articulating surfaces 76 of the medial condyle portion 72 and the lateral condyle portion 74 can define an articulating plane corresponding to the natural horizontal plane defined by the tibial condyles of a standing person.

Figure 9A:
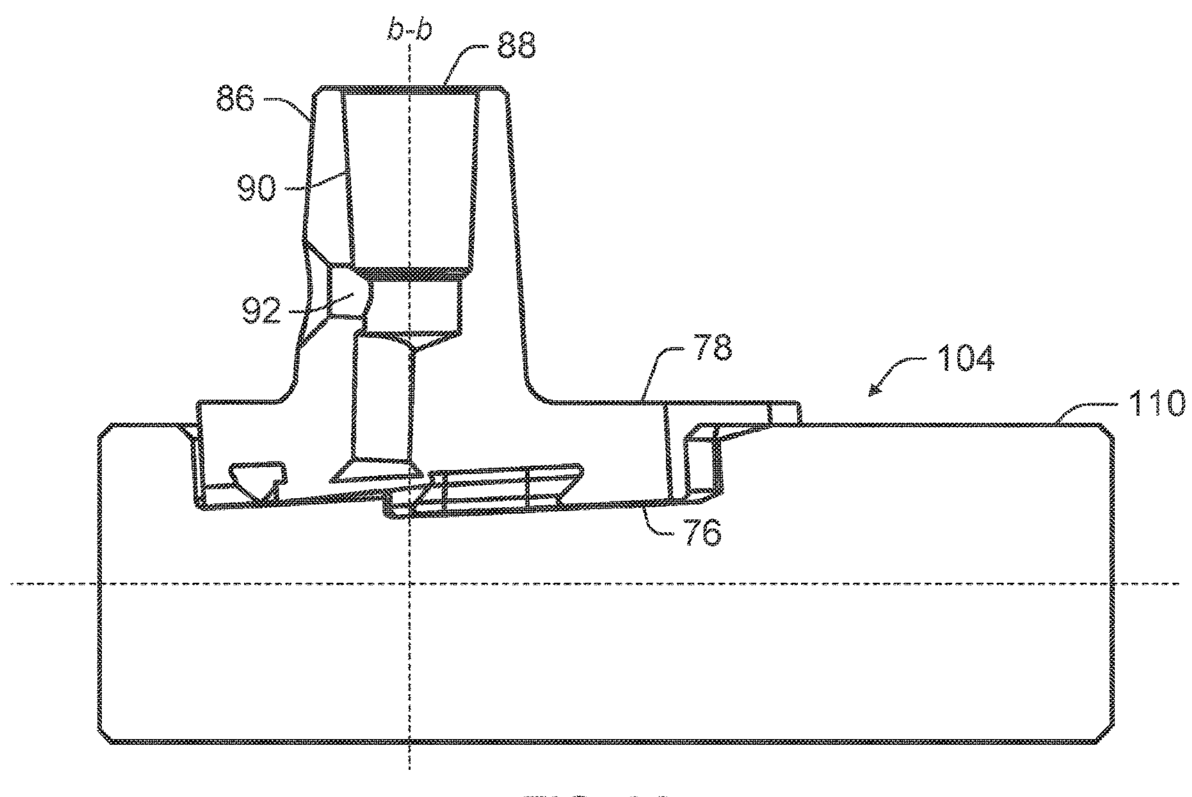
FIG. 9A is a side cross-sectional view of the impaction cradle with the tibial implant depicted in FIG. 8.
Figure 9B:
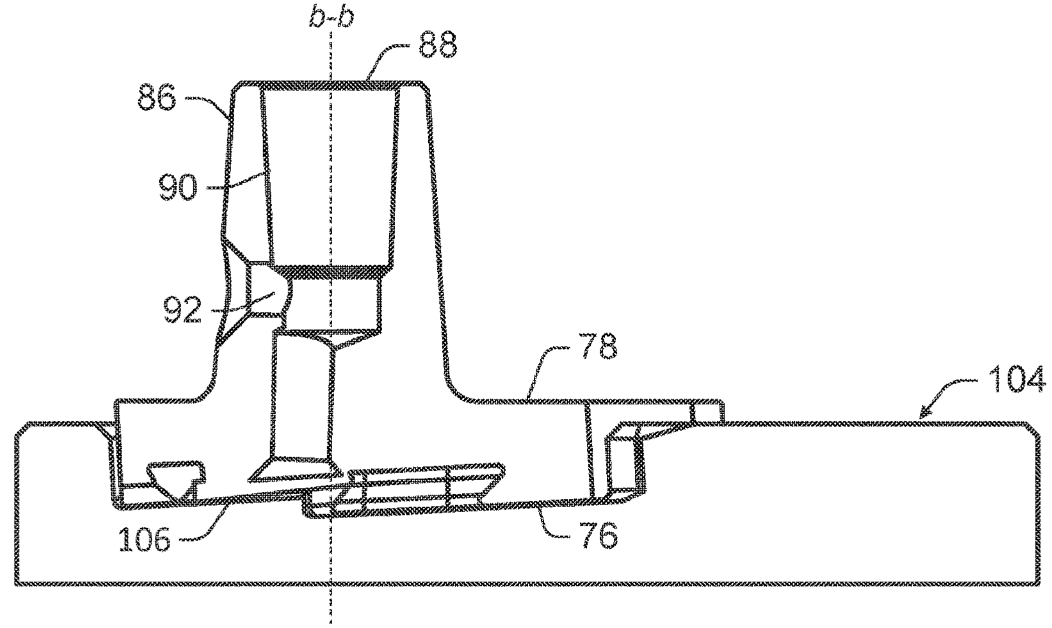
FIG. 9B is a partial side cross-sectional view of the impaction cradle with the tibial implant depicted in FIG. 9A.

As depicted in FIGS. 9A-B and 10A-B, in an embodiment, the tibial implant 70 can comprise an attachment feature 86 positioned on the bone contacting surface 78. As depicted in FIG. 9B, the attachment feature 86 can comprise an attachment port 88 defining an inner surface 90 for engaging an attachment end 42 of an intramedullary stem 40. In an embodiment, the inner surface 90 and the attachment end 42 can have corresponding Morse tapers such that the inner surface 90 frictionally engages the attachment end 42 as the intramedullary stem 40 is impacted into the attachment port 88 along an impaction axis b-b. As depicted in FIG. 9B, in an embodiment, the attachment feature 86 can comprise a detent feature 92 positioned to engage the notched portion 44 to lock the intramedullary stein 40 to the tibial implant 70. The detent feature 92 can be positioned at the bottom of the attachment port 88 to engage the notched portion 44 when the intramedullary stem 40 is fully impacted into the attachment port 88 of the tibial implant 70.

As the tibial component may have a posterior slope built in, the attachment feature 86 and attachment port 88 can be angled such that the impaction axis b-b is angled relative to the articulating surface. The angle of the impaction axis b-b can simulate the natural posterior slope of the tibia (about 3°). In an embodiment, a plurality of tibial components 70 can be provided to a medical practitioner, wherein each tibial components 70 can have an attachment port 88 oriented at a different angle to the articulating plane.

Figure 10A:
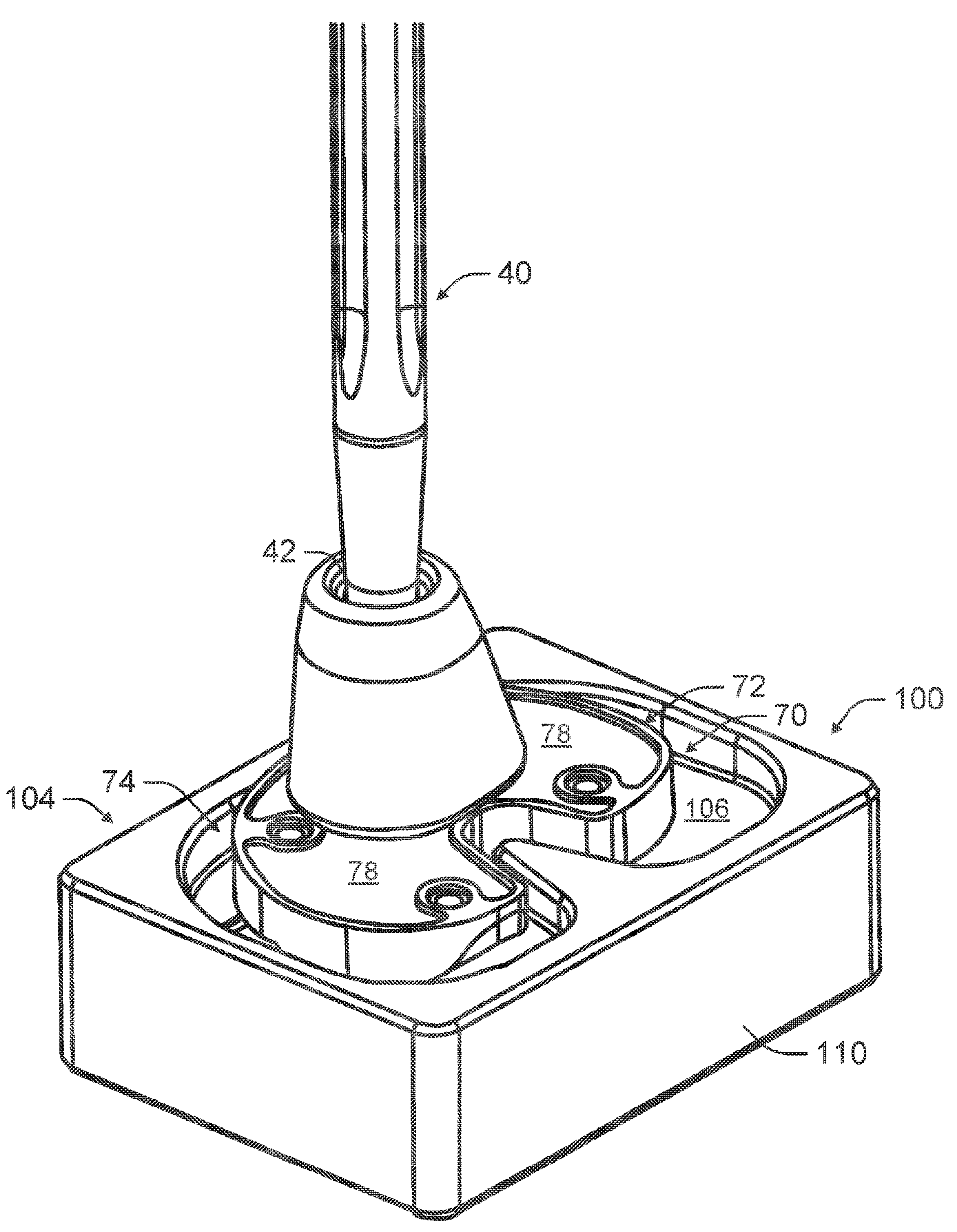
FIG. 10A is a perspective view an impaction cradle with a tibia implant resting thereon, wherein an intramedullary stem and metaphyseal sleeve are impacted onto the tibia implant according to an example of the present disclosure.
Figure 10B:
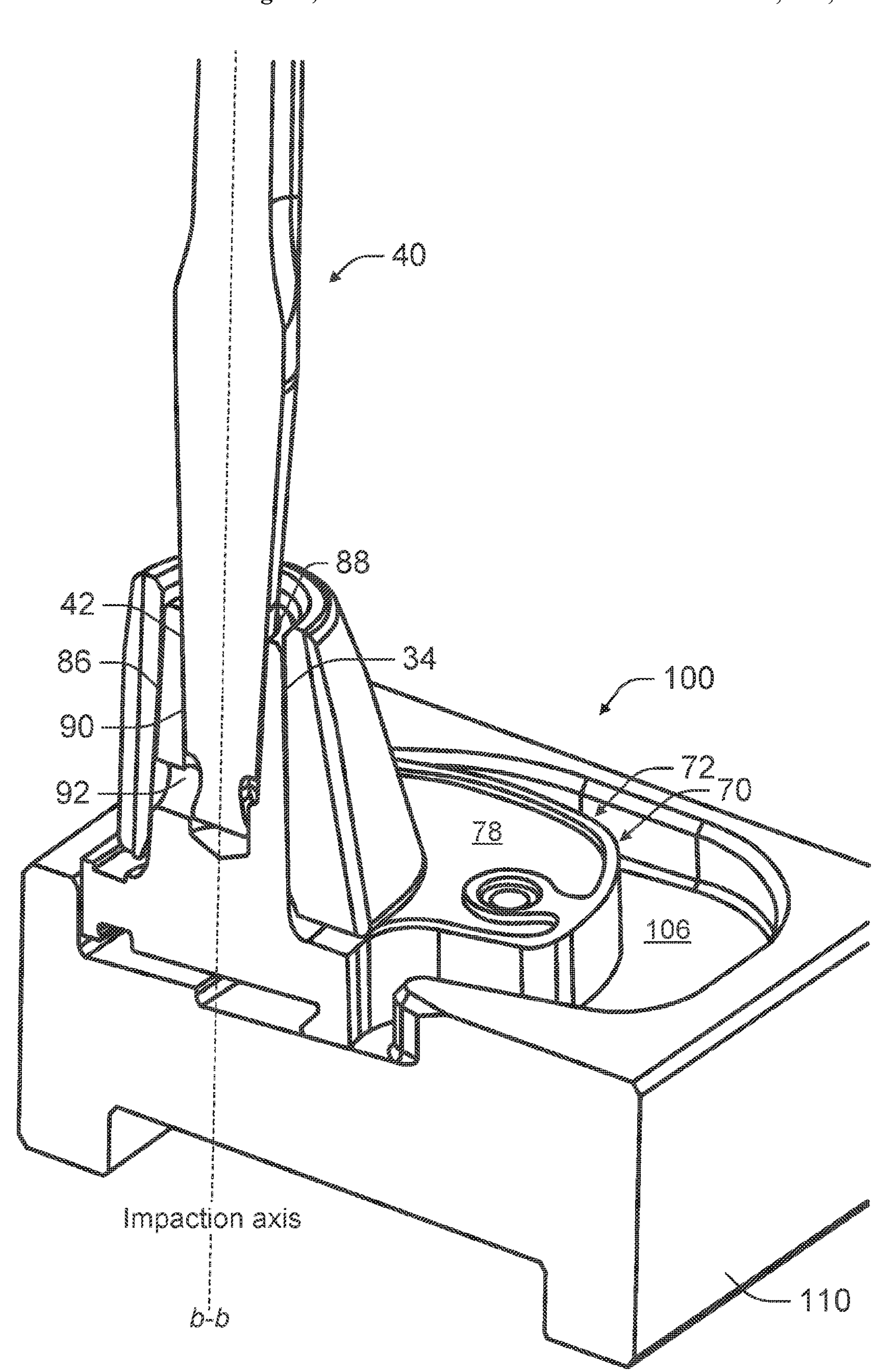
FIG. 10B is a cross-sectional perspective view the impaction cradle with the tibia implant and impacted intramedullary stem and metaphyseal sleeve depicted in FIG. 10A.

As depicted in FIGS. 10A-10B, in an embodiment, the tibial implant component 70 can include a sleeve or cone 46 positioned over an outer surface 34 of the attachment feature 86. The sleeve 46 can comprise a porous material, such as titanium, tantalum, or alloys thereof, for facilitating bone ingrowth and fixation of the tibial implant component 70.

As depicted in FIGS. 7-10B, in an embodiment, the base portion 104 can include at least one support surface 106 shaped to interface with a corresponding surface of the tibial implant 70. The support surface 106 can be shaped to interface with an articulating surface 76 of the medial condyle portion 72 or the lateral condyle portion 74 or another surface of the tibial implant 70. The support surface 106 can be angled (about 3°) to orient the articulating plane of the tibial implant 70 such that the impaction axis b-b corresponds to the natural posterior slope of the tibia In an embodiment, the support surface 106 can include at least two support surfaces 106, wherein one support surface 106 corresponds to the medial condyle portion 72 and another support surface 106 corresponds to the lateral condyle portion 74. The support surface 106 can define a support plane parallel to the articulating plane defined by medial condyle portion 72 and the lateral condyle portion 74 when the tibial implant 70 is positioned on the base portion 104.

As illustrated in FIGS. 7-10B, in an embodiment, the base portion 104 can comprise a planar body 110 defining a base plane. The base portion 104 can orient a tibial implant 70 positioned on the base portion 104 such that the support plane defined by the support surfaces 106 is oriented transverse to the base plane at the posterior slope angle. In an embodiment, the posterior slope of the support plane to the base plane is about 3° to correspond to the natural tibia. In this configuration, a tibial implant 70 positioned on the base portion 104 can be oriented such that the impaction axis b-b is parallel to a vertical axis or within a vertical plane bisecting the tibial implant 70 between the medial condyle portion 72 and the lateral condyle portion 74. The generally vertical orientation of the impaction axis b-b can reduce the difficulty of accurately impacting an intramedullary stem 40 into the attachment feature 86.

As illustrated in FIGS. 7-10B, in an embodiment, the base portion 104 can comprise a planar body 110 defining a base plane. The base portion 104 can orient a tibial implant 70 positioned on the base portion 104 such that the support plane defined by the support surfaces 106 is oriented transverse to the base plane at the varus-valgus angle. In an embodiment, the varus-valgus angle of the support plane to the base plane is about 3° to correspond to the natural subtend of the tibial anatomical axis to the vertical axis. In this configuration, a tibial implant 70 positioned on the base portion 104 can be oriented such that the impaction axis b-b is parallel to a vertical axis or within a vertical plane bisecting the tibial implant 70 between the medial condyle portion 72 and the lateral condyle portion 74. The generally vertical orientation of the impaction axis b-b can reduce the difficulty of accurately impacting an intramedullary stem 40 into the attachment feature 86.

In an example, the base portion 54 can comprise both an angled upper surface 62 corresponding to a femoral implant 10 and an angled upper surface 106 corresponding a tibial implant 70. As illustrated in FIG. 6B, the femoral angled surface 62 can be positioned on a first side of the base portion 54 and the tibial angled surface 106 can be positioned on a second side opposite to the first side. In this configuration, the base portion 54 can be reversibly positioned on the planar support surface to support either the femoral implant 10 or the tibial implant 10 depending on whether the first or section side is oriented upwards on the planar support surface. The femoral angled surface 62 and the tibial angled surface 106 can be angled to facilitate the reversal of the base portion 54. This arrangement permits a single base portion 54 to be selectively used for either the femoral implant 10 or the tibial implant 10.

VARIOUS NOTES & EXAMPLES

Example 1 is an impaction cradle for supporting a femoral implant during impaction of an intramedullary stem or metaphyseal sleeve onto an attachment feature of the femoral implant along an impaction axis, comprising: a cradle element having at least one support surface for receiving the femoral implant, the support surface defining a support plane; and a base portion having a planar body defining a base plane; wherein the cradle element is positioned on the base portion such that the cradle element is tilted to orient the support plane transverse to the base plane.

In Example 2, the subject matter of Example 1 optionally includes wherein the support plane is transverse to the base plane at a transverse angle corresponding to a varus-valgus angle of the femoral implant; wherein the transverse angle is between about 4 to about 10 degrees.

In Example 3, the subject matter of Example 2 optionally includes wherein pivoting the cradle element orients the femoral implant resting on the support surface such that the impaction axis of the femoral implant is perpendicular to the base plane.

In Example 4, the subject matter of any one or more of Examples 2-3 optionally include wherein the planar body of the base portion further comprises: an angled surface for receiving the cradle element; wherein the angled surface is oriented transverse to the base plane at the varus-valgus angle such that the support plane of the cradle element is oriented at the varus-valgus angle.

In Example 5, the subject matter of Example 4 optionally includes wherein the planar body of the base portion further comprises: a planar base surface opposite the angled surface; wherein the base surface is parallel to the base plane.

In Example 6, the subject matter of any one or more of Examples 1-5 optionally include wherein the cradle element further comprises: at least two support surfaces, wherein each support surface is positioned to engage an articulating surface of one condyle portion of the femoral implant.

In Example 7, the subject matter of Example 6 optionally includes wherein the cradle element further comprises: a stabilizing post extending between the two support surfaces; wherein the stabilizing post is receivable between the condyle portions of the femoral implant to maintain the femoral implant on the cradle element.

Example 8 is a femoral implant system, comprising: a femoral implant having an attachment feature; an intramedullary stem configured to be impacted into the attachment port along an impaction axis; and an impaction cradle, comprising: a cradle element having at least one support surface for receiving the femoral implant, the support surface defining a support plane; and a base portion having a planar body defining a base plane; wherein the cradle element is positioned on the base portion such that the cradle element is tilted to orient the support plane transverse to the base plane to orient the femoral implant such that the impaction axis is generally vertical.

In Example 9, the subject matter of Example 8 optionally includes the femoral implant further comprising: a medial femoral condyle portion comprising a medial articulating surface; and a lateral femoral condyle comprising a lateral articulating surface; wherein the medial articulating surface and the lateral articulating surface cooperate to define an articulating plane.

In Example 10, the subject matter of Example 9 optionally includes wherein the support plane is transverse to the base plane at a transverse angle corresponding to a varus-valgus angle of the femoral implant; wherein the transverse angle is between about 4 to about 10 degrees.

In Example 11, the subject matter of Example 10 optionally includes wherein the articulating plane is parallel to the support plane when the femoral implant is received on the cradle element.

In Example 12, the subject matter of any one or more of Examples 10-11 optionally include wherein the planar body of the base portion further comprises: a planar base surface opposite the angled surface; wherein the base surface is parallel to the base plane.

In Example 13, the subject matter of Example 12 optionally includes wherein the planar body of the base portion further comprises: a planar base surface opposite the angled surface; wherein the base surface is parallel to the base plane.

In Example 14, the subject matter of any one or more of Examples 9-13 optionally include wherein the cradle element further comprises: at least two support surfaces, wherein each support surface is positioned to engage an articulating surface of one condyle portion of the femoral implant.

In Example 15, the subject matter of any one or more of Examples 9-14 optionally include wherein the cradle element further comprises: a stabilizing post positioned between the two support surfaces; wherein the stabilizing post is receivable between the condyle portions of the femoral implant to main the femoral implant on the cradle element.

Example 16 is an impaction cradle for supporting a tibial implant during impaction of an intramedullary stem into an attachment port of the tibial implant along an impaction axis, comprising: a base portion having a planar body defining a base plane, the planar body further comprising an angled surface oriented transverse to the base plane.

In Example 17, the subject matter of Example 16 optionally includes wherein the angled surface is transverse to the base plane at a transverse angle corresponding to a posterior slope of the tibial implant; wherein the transverse angle is about 3 degrees.

In Example 18, the subject matter of Example 17 optionally includes wherein pivoting the cradle element orients the tibial implant resting on the support surface such that the impaction axis of the tibial implant is perpendicular to the base plane.

In Example 19, the subject matter of any one or more of Examples 16-18 optionally include wherein the planar body of the base portion further comprises: a base surface opposite the angled surface; wherein the base surface is parallel to the base plane.

Example 20 is a tibial implant system, comprising: a tibial implant having an attachment port; an intramedullary stem configured to be impacted into the attachment port along an impaction axis; and an impaction cradle, comprising: a base portion having a planar body defining a base plane, the planar body further comprising an angled surface oriented transverse to the base plane to orient the tibial implant such that the impaction axis is generally vertical.

In Example 21, the subject matter of Example 20 optionally includes wherein the tibial implant further comprises: a medial tibial condyle portion comprising a medial articulating surface; and a lateral tibial condyle comprising a lateral articulating surface; wherein the medial articulating surface and the lateral articulating surface cooperate to define an articulating plane.

In Example 22, the subject matter of Example 21 optionally includes wherein the angled surface is transverse to the base plane at a transverse angle corresponding to a posterior slope of the tibial implant; wherein the transverse angle is about 3 degrees.

In Example 23, the subject matter of any one or more of Examples 21-22 optionally include wherein the articulating plane is parallel to the support plane when the femoral implant is received on the cradle element.

In Example 24, the subject matter of any one or more of Examples 20-23 optionally include wherein pivoting the cradle element orients the tibial implant resting on the support surface such that the impaction axis of the tibial implant is perpendicular to the base plane.

In Example 25, the subject matter of any one or more of Examples 20-24 optionally include wherein the planar body of the base portion further comprises: a base surface opposite the angled surface; wherein the base surface is parallel to the base plane.

Example 26 is a knee implant system, comprising: a femoral implant having a femoral attachment feature; a femoral intramedullary stem configured to be impacted into the femoral attachment port along a femoral impaction axis; a tibial implant having a tibial attachment port; a tibial intramedullary stem configured to be impacted into the tibial attachment port along a tibial impaction axis; an impaction cradle, comprising: a cradle element having at least one femoral support surface for receiving the femoral implant, the femoral support surface defining a femoral support plane; and a base portion having a femoral angled surface for receiving the cradle element and a tibial angled surface for receiving the tibial implant; wherein the femoral angled surface is oriented transverse to the base plane at the varus-valgus angle such that the support plane of the cradle element is oriented at the transverse angle; wherein the tibial angled surface oriented transverse to the base plane to orient the tibial implant such that the impaction axis is generally vertical.

In Example 27, the subject matter of Example 26 optionally includes wherein the femoral support plane is transverse to the base plane at a transverse angle corresponding to a varus-valgus angle of the femoral implant; wherein the transverse angle is between about 4 to about 10 degrees.

In Example 28, the subject matter of Example 27 optionally includes wherein pivoting the cradle element orients the femoral implant resting on the support surface such that the impaction axis of the femoral implant is perpendicular to the base plane.

In Example 29, the subject matter of Example 28 optionally includes wherein the planar body of the base portion further comprises: a femoral planar base surface opposite the femoral angled surface; wherein the femoral planar base surface is parallel to the base plane.

In Example 30, the subject matter of Example 29 optionally includes wherein the cradle element further comprises: at least two support surfaces, wherein each support surface is positioned to engage an articulating surface of one condyle portion of the femoral implant.

In Example 31, the subject matter of Example 30 optionally includes wherein the cradle element further comprises: a stabilizing post extending between the two support surfaces; wherein the stabilizing post is receivable between the condyle portions of the femoral implant to maintain the femoral implant on the cradle element.

In Example 32, the subject matter of any one or more of Examples 26-31 optionally include wherein the angled surface is transverse to the base plane at a transverse angle corresponding to a posterior slope of the tibial implant; wherein the transverse angle is about 3 degrees.

In Example 33, the subject matter of Example 32 optionally includes wherein pivoting the cradle element orients the tibial implant resting on the support surface such that the impaction axis of the tibial implant is perpendicular to the base plane.

In Example 34, the subject matter of any one or more of Examples 26-33 optionally include wherein the planar body of the base portion further comprises: a tibial base surface opposite the tibial angled surface; wherein the tibial base surface is parallel to the base plane.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the present subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the present subject matter should be determined with reference to the appended claims, along with the full scope of equivalents to which such claims are entitled.

What is claimed is:

1. An impaction cradle for supporting a tibial implant during impaction of an intramedullary stem into an attachment port of the tibial implant along an impaction axis, comprising:

a rectangular base defining a rectangular outer perimeter and having a planar body defining a base plane, the planar body further comprising a top surface, an angled surface recessed from the top surface and oriented transverse to the base plane, and a base surface opposite the angled surface, the angled surface including a first recessed planar segment and a second stepped recessed planar segment that lies closer to the top surface of the planar body than the first recessed planar segment;

wherein the top surface and the base surface are parallel to the base plane;

wherein the angled surface is transverse to the base plane at a transverse angle of about 3 degrees corresponding to a posterior slope of the tibial implant; and wherein the angled surface is shaped to receive a lateral condyle portion and a medial condyle portion of the tibial implant.

2. The impaction cradle of claim 1, wherein the angled surface is recessed from a top surface of the planar body.

3. The impaction cradle of claim 2, wherein the top surface is substantially parallel to the base surface.

4. The impaction cradle of claim 3, wherein the planar body further comprises a second angled surface recessed from the base surface, the second angled surface configured to receive a cradle element for a femoral implant.

5. The impaction cradle of claim 1, wherein the angled surface is shaped to receive and be in contact with a medial articulating surface of the tibial implant and a lateral articulating surface of the tibial implant.

6. A tibial implant system, comprising:

a tibial implant having an attachment port;

an intramedullary stem configured to be impacted into the attachment port along an impaction axis; and an impaction cradle, comprising:

a rectangular base defining a rectangular perimeter and having a planar body including an upper planar surface defining a base plane and a lower planar surface opposite the upper planar surface and parallel thereto, the planar body further comprising an angled surface recessed from the upper planar surface and oriented transverse to the base plane to orient the tibial implant such that the impaction axis is generally vertical, the angled surface including a first recessed planar segment and a second stepped recessed planar segment that lies closer to the upper planar surface of the planar body than the first recessed planar segment, wherein the angled surface is shaped to receive a lateral tibial condyle portion and a medial tibial condyle portion of the tibial implant.

7. The tibial implant system of claim 6, wherein:

the medial tibial condyle portion comprises a medial articulating surface; and the lateral tibial condyle portion comprises a lateral articulating surface;

wherein the medial articulating surface and the lateral articulating surface cooperate to define an articulating plane.

8. The tibial implant system of claim 7, wherein the angled surface is transverse to the base plane at a transverse angle corresponding to a posterior slope of the tibial implant.

9. The tibial implant system of claim 8, wherein the transverse angle is about 3 degrees.

10. The tibial implant system of claim 7, wherein the articulating plane is parallel to the angled surface when the tibial implant is received on the impaction cradle.

11. The tibial implant system of claim 6, wherein the tibial implant includes a detent located within the attachment port.

12. The tibial implant system of claim 11, wherein the intramedullary stem includes a notched portion configured to engage the detent to lock the intramedullary stem to the tibial implant.

13. A knee implant system, comprising:

a tibial implant having a tibial attachment port;

a tibial intramedullary stem configured to be impacted into the tibial attachment port along a tibial impaction axis; and an impaction cradle, comprising:

a rectangular base defining a rectangular outer perimeter and having a planar body including an upper planar surface defining a base plane, a lower planar surface opposite the upper planar surface and parallel thereto, a tibial angled surface recessed from the upper planar surface for receiving the tibial implant, and a femoral angled surface for receiving a cradle element;

wherein the tibial angled surface is oriented transverse to the base plane to orient the tibial implant such that the impaction axis is generally vertical;

wherein the tibial angled surface includes a first recessed planar segment and a second stepped recessed planar segment that lies closer to the upper planar surface of the planar body than the first recessed planar segment.

14. The knee implant system of claim 13, wherein the impaction cradle further comprises:

a cradle element having at least one femoral support surface for receiving a femoral implant, the femoral support surface defining a femoral support plane.

15. The knee implant system of claim 14, further comprising:

a femoral implant having a femoral attachment port; and a femoral intramedullary stem configured to be impacted into the femoral attachment port along a femoral impaction axis.

* * * * *